(12) United States Patent
Moffitt et al.

(10) Patent No.: US 8,965,515 B2
(45) Date of Patent: Feb. 24, 2015

(54) SYSTEMS AND METHODS FOR MAKING AND USING IMPROVED LEAD EXTENSION CONNECTORS FOR ELECTRICAL STIMULATION SYSTEMS

(75) Inventors: Michael Adam Moffitt, Valencia, CA (US); Courtney Lane, Ventura, CA (US); John Michael Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 295 days.

(21) Appl. No.: 13/368,666

(22) Filed: Feb. 8, 2012

(65) Prior Publication Data

US 2012/0203302 A1 Aug. 9, 2012

Related U.S. Application Data

(60) Provisional application No. 61/440,689, filed on Feb. 8, 2011.

(51) Int. Cl.
*A61N 1/00* (2006.01)
*A61N 1/05* (2006.01)

(52) U.S. Cl.
CPC .............. *A61N 1/0529* (2013.01); *A61N 1/0534* (2013.01); *A61N 1/0558* (2013.01)
USPC ................. 607/45; 607/116; 607/37

(58) Field of Classification Search
CPC .. A61N 1/0529; A61N 1/0558; A61N 1/3752
USPC ....................................... 607/116–118, 37–38
See application file for complete search history.

(56) References Cited

U.S. PATENT DOCUMENTS

| 7,809,446 | B2 | 10/2010 | Meadows |
| 7,904,161 | B2* | 3/2011 | Osypka ........................... 607/37 |
| 2003/0125786 | A1* | 7/2003 | Gliner et al. ................... 607/116 |
| 2007/0150036 | A1 | 6/2007 | Anderson |
| 2009/0187222 | A1 | 7/2009 | Barker |
| 2009/0276021 | A1 | 11/2009 | Meadows |
| 2010/0076535 | A1 | 3/2010 | Pianca |
| 2011/0098782 | A1* | 4/2011 | Kast et al. ....................... 607/46 |

OTHER PUBLICATIONS

U.S. Appl. No. 12/177,823, filed Jul. 22, 2008.

* cited by examiner

*Primary Examiner* — Michael Kahelin
*Assistant Examiner* — Mallika D Fairchild
(74) *Attorney, Agent, or Firm* — Lowe Graham Jones PLLC; Bruce E. Black

(57) ABSTRACT

A lead extension for an electrical stimulation system includes a connector disposed on a first end of a body. The connector includes a housing defining at least one port. Each of the at least one ports is configured to receive a proximal end of a lead. A plurality of connector contacts are disposed in each of the at least one ports. The connector contacts are configured to electrically couple to terminals of a lead when the lead is received by the housing. A first connector flange extends outwardly from a first side of the housing. A plurality of conductors extend along a length of the lead extension and electrically couple at least one of the connector contacts to at least one terminal disposed on a second end of the body.

19 Claims, 6 Drawing Sheets

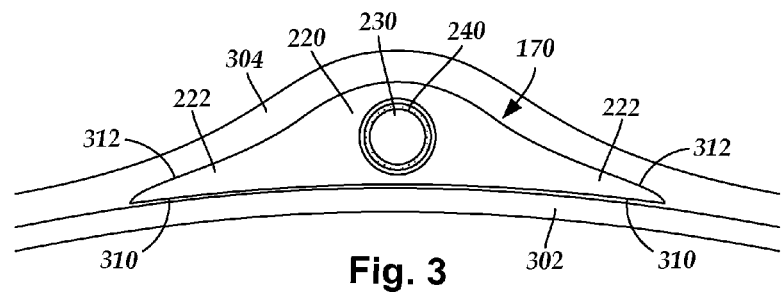
Fig. 3
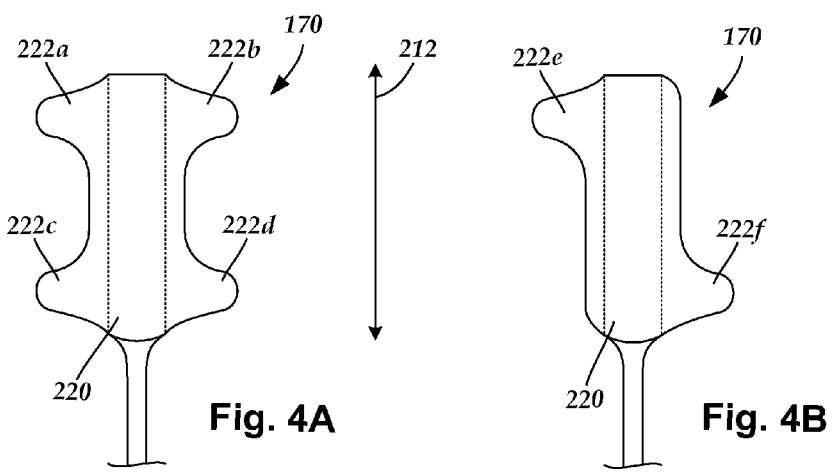
Fig. 4A   Fig. 4B
Fig. 4C

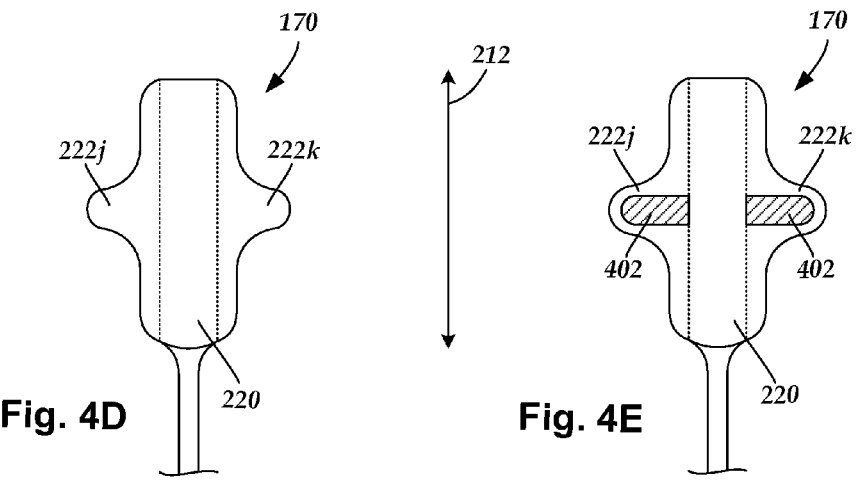
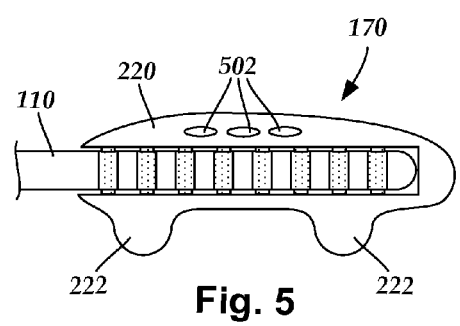
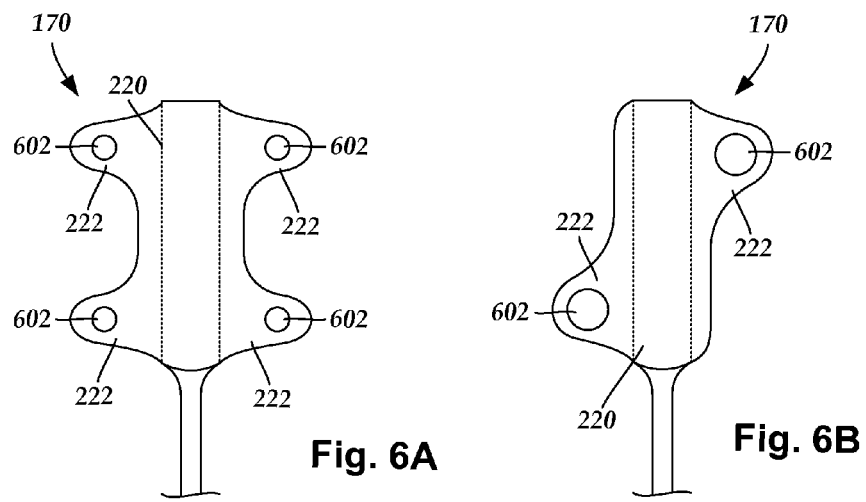

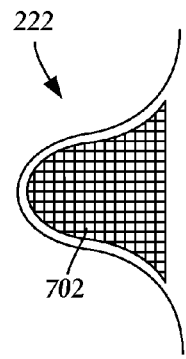
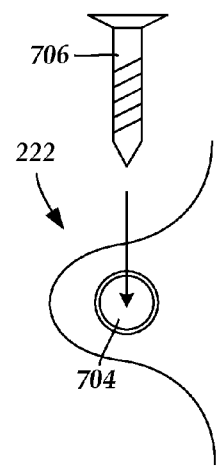
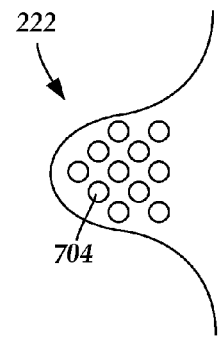
Fig. 7A
Fig. 7B
Fig. 7C
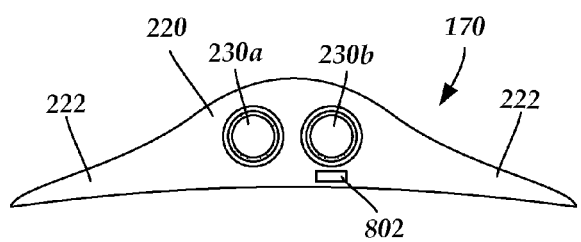
Fig. 8A

SYSTEMS AND METHODS FOR MAKING AND USING IMPROVED LEAD EXTENSION CONNECTORS FOR ELECTRICAL STIMULATION SYSTEMS

CROSS-REFERENCE TO RELATED APPLICATIONS

This application claims the benefit under 35 U.S.C. §119(e) of U.S. Provisional Patent Application Ser. No. 61/440,689 filed on Feb. 8, 2011, which is incorporated herein by reference.

FIELD

The invention is directed to the area of electrical stimulation systems and methods of making and using the systems. The present invention is also directed to electrical stimulation lead extensions having improved connectors for stabilizing and securing the lead extensions to patient tissue, as well as methods of making and using the connectors, lead extensions, and electrical stimulation systems.

BACKGROUND

Electrical Stimulation can be useful for treating a variety of conditions. Deep brain stimulation can be useful for treating, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

BRIEF SUMMARY

In one embodiment, a lead extension for an electrical stimulation system includes a lead extension body having a first end and an opposing second end. The lead extension body includes at least one tail. A plurality of lead extension terminals are disposed on the second end of the lead extension body such that at least one of the plurality of lead extension terminals is disposed on each of the at least one tails. A connector is disposed at the first end of the lead extension body. The connector has a first side and an opposing second side. The connector includes a connector housing defining at least one connector port at one end of the connector housing. Each of the at least one connector ports is configured and arranged to receive a proximal end of a lead. A plurality of connector contacts are disposed in the connector port. The connector contacts are configured and arranged to electrically couple to terminals of a lead when the lead is received by the connector housing. A first connector flange extends outwardly from the first side of the connector housing. A plurality of conductors extend along a length of the lead extension body. Each of the conductors electrically couples at least one of the lead extension terminals to at least one of the plurality of connector contacts.

In another embodiment, an electrical stimulation system includes a lead extension, a lead, and a control unit. The lead extension includes a lead extension body having a first end and an opposing second end. The lead extension body includes at least one tail. A plurality of lead extension terminals are disposed on the second end of the lead extension body such that at least one of the plurality of lead extension terminals is disposed on each of the at least one tails. A connector is disposed at the first end of the lead extension body. The connector has a first side and an opposing second side. The connector includes a connector housing defining at least one connector port at one end of the connector housing. Each of the at least one connector ports is configured and arranged to receive a proximal end of a lead. A plurality of connector contacts are disposed in the connector port. The connector contacts are configured and arranged to electrically couple to terminals of a lead when the lead is received by the connector housing. A first connector flange extends outwardly from the first side of the connector housing. A plurality of conductors extend along a length of the lead extension body. Each of the conductors electrically couples at least one of the lead extension terminals to at least one of the plurality of connector contacts. The lead is configured and arranged for insertion into the at least one connector port of the lead extension. The lead includes a lead body having a distal end, a proximal end, and a longitudinal length; a plurality of electrodes disposed on the distal end of the lead body; a plurality of lead terminals disposed on the proximal end of the lead body; and a plurality of conductors electrically coupling at least one of the electrodes to at least one of the lead terminals. The plurality of conductors extend along the longitudinal length of the lead body. The control unit is coupleable to the second end of the lead extension body. The control unit is configured and arranged for providing stimulation to the plurality of electrodes of the lead.

In yet another embodiment, a method for stimulating patient tissue includes providing an electrical stimulation system. The electrical stimulation system includes a lead extension, a lead, and a control unit. The lead extension includes a lead extension body having a first end and an opposing second end. The lead extension body includes at least one tail. A plurality of lead extension terminals are disposed on the second end of the lead extension body such that at least one of the plurality of lead extension terminals is disposed on each of the at least one tails. A connector is disposed at the first end of the lead extension body. The connector has a first side and an opposing second side. The connector includes a connector housing defining at least one connector port at one end of the connector housing. Each of the at least one connector ports is configured and arranged to receive a proximal end of a lead. A plurality of connector contacts are disposed in the connector port. The connector contacts are configured and arranged to electrically couple to terminals of a lead when the lead is received by the connector housing. A first connector flange extends outwardly from the first side of the connector housing. A plurality of conductors extend along a length of the lead extension body. Each of the conductors electrically couples at least one of the lead extension terminals to at least one of the plurality of connector contacts. The lead is configured and arranged for insertion into the at least one connector port of the lead extension. The lead includes a lead body having a distal end, a proximal end, and a longitudinal length; a plurality of electrodes disposed on the distal end of the lead body; a plurality of lead terminals disposed on the proximal end of the lead body; and a plurality of conductors electrically coupling at least one of the electrodes to at least one of the lead terminals. The plurality of conductors extend along the longitudinal length of the lead body. The control unit is coupleable to the second end of the lead extension body. The control unit is configured and arranged for providing stimulation to the plurality of electrodes of the lead. The lead of the electrical stimulation system is partially inserted within the skull of a patient such that the electrodes of the lead are within the patient's skull and the terminals of the lead are external to the skull. The lead extension connector of the electrical stimulation system is disposed over the patient's skull such that the first connector flange lies flat against the patient's skull. The terminals of the lead are inserted into the at least one connector port of the lead extension connector. The second end of the lead extension body is coupled to the control unit. Patient tissue is stimulated using the electrodes of the lead using electrical pulses generated within the control unit.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 3 is a schematic transverse cross-sectional view of one embodiment of the connector of FIG. 1 disposed over a portion of a patient's skull, according to the invention;

FIG. 4A is a schematic top view of one embodiment of the connector of FIG. 1, the connector including connector flanges extending outwardly from opposing sides of a connector housing, according to the invention;

FIG. 4B is a schematic top view of a second embodiment of the connector of FIG. 1, the connector including connector flanges extending outwardly from opposing sides of a connector housing, according to the invention;

FIG. 4C is a schematic top view of a third embodiment of the connector of FIG. 1, the connector including connector flanges extending outwardly from opposing sides of a connector housing, according to the invention;

FIG. 4D is a schematic top view of a fourth embodiment of the connector of FIG. 1, the connector including connector flanges extending outwardly from opposing sides of a connector housing, according to the invention;

FIG. 4E is a schematic top view of another embodiment of the connector of FIG. 4D, the connector including support members disposed on connector flanges for providing increased rigidity to the connector flanges, according to the invention;

FIG. 5 is a schematic longitudinal cross-sectional view of one embodiment of the connector of FIG. 1, the connector including one or more tissue-coupling elements defined in a connector housing, the tissue-coupling elements for promoting tissue ingrowth, according to the invention;

FIG. 6A is a schematic top view of one embodiment of the connector of FIG. 1, the connector including a tissue-coupling element formed as an aperture defined in each of a plurality of connector flanges extending outwardly from opposing sides of a connector housing, according to the invention;

FIG. 6B is a schematic top view of another embodiment of the connector of FIG. 1, the connector including a tissue-coupling element formed as an aperture defined in each of a plurality of connector flanges extending outwardly from opposing sides of a connector housing, according to the invention;

FIG. 7A is a schematic top close-up view of one embodiment of a connector flange of the connector of FIG. 1, the connector flange including a tissue-coupling element formed as a mesh matrix, according to the invention;

FIG. 7B is a schematic top close-up view of one embodiment of a connector flange of the connector of FIG. 1, the connector flange including a tissue-coupling element formed as a ring configured and arranged for receiving a fastener, according to the invention;

FIG. 7C is a schematic top close-up view of one embodiment of a connector flange of the connector of FIG. 1, the connector flange including tissue-coupling elements for promoting tissue ingrowth, according to the invention;

FIG. 8A is a schematic transverse cross-sectional view of another embodiment of the connector of FIG. 1, the connector including a connector housing configured and arranged to receive proximal ends of multiple leads, according to the invention;

DETAILED DESCRIPTION

The invention is directed to the area of electrical stimulation systems and methods of making and using the systems. The present invention is also directed to electrical stimulation lead extensions having improved connectors for stabilizing and securing the lead extensions to patient tissue, as well as methods of making and using the connectors, lead extensions, and electrical stimulation systems.

A lead for deep brain stimulation may include stimulation electrodes, recording electrodes, or a combination of both. A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes.

Deep brain stimulation devices and leads are described in, for example, U.S. Pat. No. 7,809,446 ("Devices and Methods For Brain Stimulation"), U.S. Patent Application Publication No. 2010/0076535 A1 ("Leads With Non-Circular-Shaped Distal Ends For Brain Stimulation Systems and Methods of Making and Using"), U.S. Patent Application Publication 2007/0150036 A1 ("Stimulator Leads and Methods For Lead Fabrication"), U.S. patent application Ser. No. 12/177,823 ("Lead With Transition and Methods of Manufacture and Use"), U.S. Patent Application Publication No. 2009/0276021 A1 ("Electrodes For Stimulation Leads and Methods of Manufacture and Use"), U.S. Patent Application Ser. No. 61/170,037 ("Deep Brain Stimulation Current Steering with Split Electrodes"), U.S. Patent Application Ser. No. 61/022,953, U.S. Patent Application Ser. No. 61/316,759, U.S. Patent Application Publication No. 2009/0187222 A1. Each of these references is incorporated herein by reference in its respective entirety.

Figure 1:
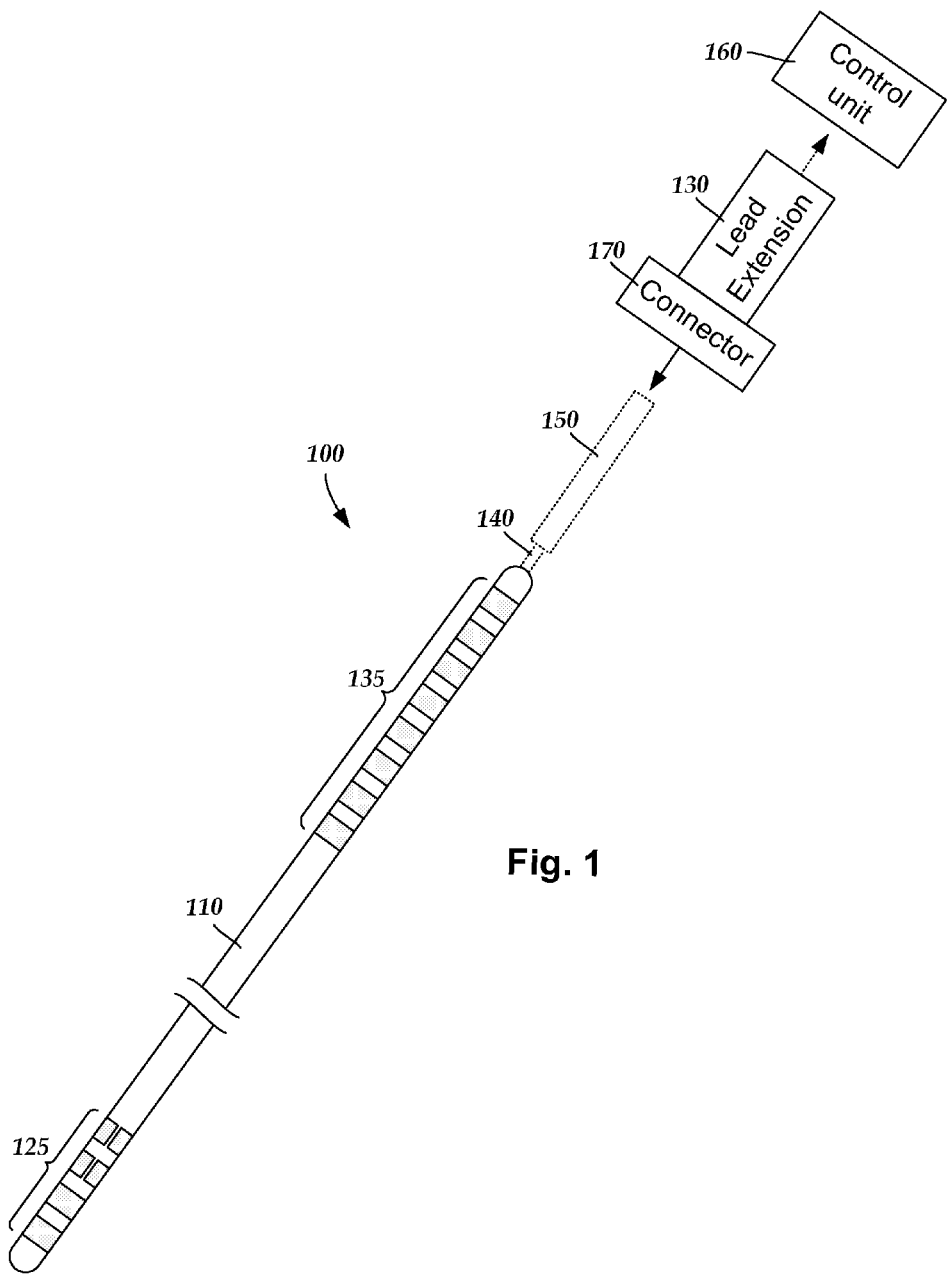
FIG. 1 is a schematic side view of one embodiment of a brain stimulation system that includes a lead, a lead extension, and a control unit, according to the invention.

FIG. 1 illustrates one embodiment of an electrical stimulation system 100 for brain stimulation. The electrical stimulation system 100 includes a lead 110, a plurality of electrodes 125 disposed at least partially about a circumference of the lead 110, a plurality of terminals 135, a lead extension 130 for connection of the electrodes 125 to a control unit 160, and a stylet 140 for assisting in insertion and positioning of the lead 110 in the patient's brain. It may be advantageous to include the lead extensions 130 to prevent having to remove or replace the lead 110 if the proximal end of the lead 110 fails due to fatigue (e.g., from flexing of the patient's neck, or the like).

The stylet 140 can be made of a rigid material. Examples of suitable materials include tungsten, stainless steel, or plastic. The stylet 140 may have a handle 150 to assist insertion into the lead 110, as well as rotation of the stylet 140 and lead 110. The lead extension 130 includes a connector 170 that fits over a proximal end of the lead 110, preferably after removal of the stylet 140.

The control unit 160 is typically an implantable pulse generator that can be implanted into a patient's body, for example, below the patient's clavicle area. The pulse generator can have eight stimulation channels which may be independently programmable to control the magnitude of the current stimulus from each channel. In some cases, the pulse generator may have more than eight stimulation channels (e.g., 16-, 32-, or more stimulation channels). The control unit 160 may have one, two, three, four, or more connector ports, for receiving the plurality of terminals 135 at the proximal end of the lead 110.

In one example of operation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of the stylet 140.

The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 110 for deep brain stimulation can include stimulation electrodes, recording electrodes, or both. In at least some embodiments, the lead 110 has a cross-sectional diameter of no more than 1.5 mm and may be in the range of 1 to 1.5 mm. In at least some embodiments, the lead 110 is rotatable so that the stimulation electrodes can be aligned with the target neurons after the neurons have been located using the recording electrodes. Stimulation electrodes may be disposed on the circumference of the lead 110 to stimulate the target neurons. Stimulation electrodes may be ring-shaped or segmented.

The lead extension 130 typically couples the electrodes 125 to the control unit 160 (which typically houses a pulse generator that supplies electrical signals to the electrodes 125). Connectors of conventional lead extensions are typically disposed within patient tissue such that the connectors are disposed over the patient's skull and beneath or within the patient's scalp above one of the patient's ear. It is typically preferred to reduce the diameter of the connector extending outward from the patient's skull due to the tightness of skin in the region of implantation, and also for cosmetic reasons.

Over time after implantation, patient skin disposed over conventional lead extensions (and in particular over conventional lead-extension connectors) may begin to erode due to the size of connectors extending outwards from the patient's skull, the tightness of skin over the connector, and the potential mobility (e.g., rotational, translational, or the like) of the conventional lead extensions relative to the patient during patient activity. Additionally, the mobility of conventional lead extensions relative to patient movement may also cause lead extension failure (e.g., electrical disconnection). One technique that has previously been used for reducing these adverse effects is to carve out portions of the patient's scalp or skull to form one or more recesses; position the connector or one or more portions of the lead extension in the one or more recesses; and suture the connector or lead extension to surrounding periosteum or scalp tissue. Carving out one or more recesses, however, can be labor intensive and invasive.

As herein described, a connector can be configured and arranged to facilitate a reduction of at least one of skin erosion and lead extension failure. The connector flanges can take advantage of the anatomy of the region of implantation, where although the tightness of patient skin discourages the connectors from extending very far outward from the patient's skull, there is often ample space to extend the connectors outward along the surface of the patient's skull. The connector includes one or more connector flanges that extend from one or more sides of the connector along the patient's skull. The one or more connector flanges stabilize the orientation of the connector. For example, the one or more connector flanges may prevent the connector from rotating about a longitudinal length of the connector. The one or more connector flanges may also provide a surface for securing the connector to the patient without needing to suture the connector housing.

Figures 2A, 2B, 2C:
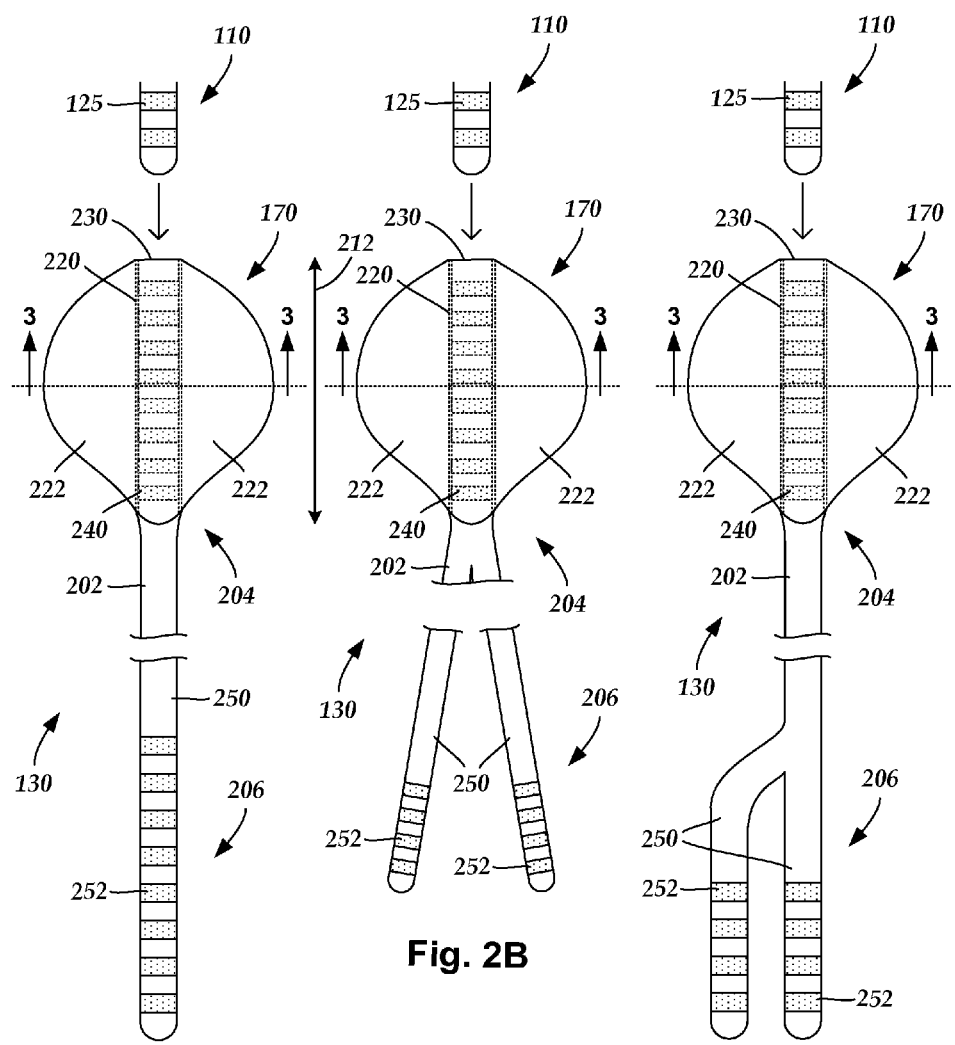
FIG. 2A is a schematic top view of one embodiment of a portion of the lead extension and connector of FIG. 1, the connector suitable for receiving the proximal end of the lead of FIG. 1, according to the invention.
FIG. 2B is a schematic top view of another embodiment of a portion of the lead extension and connector of FIG. 1, the connector suitable for receiving the proximal end of the lead of FIG. 1, according to the invention.
FIG. 2C is a schematic top view of yet another embodiment of a portion of the lead extension and connector of FIG. 1, the connector suitable for receiving the proximal end of the lead of FIG. 1, according to the invention.

FIGS. 2A-2C are schematic top views of several embodiments of the lead extension 130. FIG. 3 is a schematic transverse cross-sectional view of one embodiment of the connector 170 disposed over a skull 302 and within a scalp 304 of a patient. The lead extension 130 includes a lead extension body 202 having a first end 204 and a second end 206 opposite to the first end 204. The connector 170 is disposed at the first end 204 of the lead extension body 202. The connector 170 has a longitudinal length 212 and includes a connector housing 220 and one or more substantially-flat connector flanges 222 extending from opposing sides of the connector housing 220 along portions of the longitudinal length 212 of the connector 170.

One end of the connector housing 220 defines a connector port 230 suitable for receiving the proximal end of the lead 110. A plurality of connector contacts, such as connector contact 240, are disposed in the connector port 230 and are coupled to conductors (not shown) that extend to the second end 206 of the lead extension body 202. The conductors may extend through the material of the lead extension 130 or along one or more lumens defined by the lead extension 130, or both. The connector contacts 240 are configured and arranged to align with the terminals 135 of the lead 110 when the lead 110 is inserted into the connector port 230.

One or more tails 250 are disposed at the second end 206 of the lead extension body 202. Lead extension terminals, such as lead extension terminal 252, are disposed on each of the one or more tails 250. The tails 250 are configured and arranged for coupling with the control unit 160. Any suitable number of tails 250 can be employed (e.g., one, two, three, four, five, six, seven, eight, or more). FIGS. 2A-2C show several exemplary configurations. In FIG. 2A, a single tail 250 is disposed at the second end 206 of the lead extension 130. In FIG. 2B, a plurality of tails 250 are disposed at the second end 206 of the lead extension 130. In FIG. 2C, the lead extension 130 includes a single tail that couples to the connector 170 and that splits into a plurality of tails 250.

As shown in FIG. 3, the connector 170 is positioned against the patient such that both of the connector flanges 222 extend along the patient's skull 302. The connector flanges 222 each include a first major surface 310 and an opposing second major surface 312. One or more of the first major surfaces 310 can be concave along one or more axes to improve the fit between the connector flanges and the patient's skull. When the connector flanges 222 are positioned against the skull 302 with one or more layers of the scalp 304 disposed thereover, the connector flanges 222 may discourage rotation of the connector 170 about an axis of the connector port 230.

In preferred embodiments, the second major surfaces 312 of the connector flanges 222 are tapered such that the lateral portions of the connector flanges are thinner than the connector housing. The tapering of the second major surfaces 312 may reduce the erosion of patient tissue (e.g., skin) over time in proximity to the connector 170 due to relative movement between the connector 170 and the patient when the patient moves.

The connector flanges 222 can have any suitably-shaped outer perimeters along the longitudinal length 212 of the connector 170. FIG. 4A is a schematic top view of one embodiment of the connector 170 including two sets of connector flanges 222a,b and 222c,d positioned on opposite sides of the connector housing 220 from one another. In FIG. 4A, the individual connector flanges within each set of connector flanges 222a,b and 222c,d are positioned directly across the connector housing 220 from one another with respect to the longitudinal length 212 of the connector 170.

The connector 170 can have any suitable number of connector flanges 222 extending outwards from the connector housing 220 including, for example, one, two, three, four, five, six, seven, eight, nine, ten, eleven, twelve, or more connector flanges 222. The connector flanges 222 can be formed from any biocompatible material(s) suitable for implantation (e.g., rigid polymers, soft polymers, or the like or combinations thereof). In some embodiments, the connector flanges are formed from one or more of silicone, polyurethane, polyetheretherketone, or the like.

The connector flanges 222 can be oriented relative to one another along the longitudinal length 212 of the connector 170 in any suitable manner. For example, (as shown in FIG. 4A) two connector flanges 222 can be disposed on opposite sides of the connector housing 220 from one another such that the two connector flanges 222 are positioned directly across the connector housing 220 from one another with respect to the longitudinal length 212 of the connector 170 (see also FIGS. 4D and 4E).

As another example, two connector flanges 222 can be disposed on opposite sides of the connector housing 220 from one another such that the two connector flanges 222 are longitudinally offset (i.e., staggered) from one another with respect to the longitudinal length 212 of the connector 170. FIG. 4B is a schematic top view of one embodiment of the connector 170 including two connector flanges 222e,f positioned on opposite sides of the connector housing 220 from one another. In FIG. 4B, the individual connector flanges within the set of connector flanges 222e,f are staggered from one another along the longitudinal length 212 of the connector 170. In FIG. 4B, the connector flanges 222e,f are longitudinally offset from one another such that the connector flanges 222e,f are positioned in proximity to opposite ends of the connector housing 220. In alternate embodiments, connector flanges can be longitudinally offset from one another such that one, or none, of the connector flanges are in proximity to either end of the connector housing 220.

As yet another example, a single connector flange 222 can be disposed on one side of the connector housing 220 such that there is no corresponding connector flange on the opposing side of the connector housing 220. It will be understood that the connector 170 may include any combination of the above exemplary arrangements. FIG. 4C is a schematic top view of one embodiment of the connector 170 including two connector flanges 222g,h positioned across the connector housing 220 from one another such that the individual connector flanges within the set of connector flanges 222g,h are staggered from one another with respect to the longitudinal length 212 of the connector 170. FIG. 4C also includes a single connector flange 222i disposed along the longitudinal length 212 of the connector 170 such that there is no corresponding connector flange on the opposing side of the connector housing 220.

FIG. 4D is a schematic top view of one embodiment of the connector 170 including a single set of connector flanges 222j,k positioned on opposite sides of the connector housing 220 from one another. In FIG. 4D, the individual connector flanges within the set of connector flanges 222j,k are positioned directly across the connector housing 220 from one another with respect to the longitudinal length 212 of the connector 170. In FIG. 4D, the connector flanges 222*j,k* are positioned in proximity to a middle of the longitudinal length 212 of the connector 170. In alternate embodiments, the connector flanges 222*j,k* are positioned in proximity to one of the ends of the connector housing 220.

When one or more of the connector flanges 222 are formed from a soft material, one or more comparatively rigid (i.e., stiffening) members can be disposed on, or in, one or more of the connector flanges 222 to provide additional rigidity to the connector flange 222, if needed, during implantation or securement of the connector 170 to the patient. The one or more stiffening members can be formed from any biocompatible material (e.g., one or more plastics, metals, alloys, or the like or combinations thereof) that provides sufficient rigidity to facilitate implantation and securement of the connector 170 to patient tissue.

FIG. 4E is a schematic top view of one embodiment of the connector 170 with the single set of connector flanges 222*j,k* positioned on opposite sides of the connector housing 220 from one another. A stiffening member 402 is disposed along portions of each of the connector flanges 222*j,k*. Alternately, the stiffening member 402 can be disposed on, or in, only one of the connector flanges 222*j,k*. The stiffening member 402 can be disposed on, or in, one or more of the connector flanges 222*j,k* in any suitable position, direction, or orientation. For example, the stiffening member 402 can extend outwardly from the connector housing 220, either orthogonally (as shown in FIG. 4E), or at other non-orthogonal angles.

It may be advantageous to form the connector flanges 222 as narrow as possible along an axis defined by the longitudinal length 212 of connector housing 220. For example, it may be more advantageous to employ the connector flanges 222 shown in one of FIGS. 4A-4E over the connector flanges 222 shown in FIGS. 2A-2C. Utilizing more longitudinally-narrow connector flanges 222 may reduce the surface area of the connector flanges 222 contacting patient tissue, thereby potentially displacing less patient tissue during implantation. Reducing the amount of displaced tissue during implantation may, consequently, cause less disruption of tissue revascularization following implantation.

Turning now to FIG. 5, the connector 170 can, optionally, be coupled to patient tissue. Coupling the connector 170 to patient tissue may decrease relative movement of the connector 170 with respect to the patient, thereby potentially reducing skin erosion, or lead extension failure, or both during patient movement. The connector 170 can couple to patient tissue via one or more tissue-coupling elements disposed on or in one or more portions of the connector 170 (e.g., the connector housing or one or more of the connector flanges).

In some embodiments, one or more of the tissue-coupling elements are designed to facilitate coupling of the connector 170 to patient tissue via tissue ingrowth. For example, the connector 170 may include one or more invaginations, apertures, or the like configured and arranged for promoting tissue ingrowth, the tissue ingrowth facilitating securing of the connector 170 to patient tissue over the implantable lifetime of the lead extension 130.

FIG. 5 is a schematic longitudinal cross-sectional view of one embodiment of the connector 170. The connector 170 includes tissue-coupling elements 502 disposed in the connector housing 220 and configured and arranged to promote tissue ingrowth over the implantable lifetime of the lead extension 130. In FIG. 5, the tissue-coupling elements 502 are formed as recesses. Optionally, one or more tissue elements 502 can be formed as one or more apertures, or the like. In FIG. 5, the tissue elements 502 are shown disposed in the connector housing 220. It will be understood that one or more tissue elements 502 can be disposed on any external surface of the connector 170, such as in one or more of the connector flanges 222 in lieu of, or in addition to, the connector housing 220.

Turning to FIG. 6A, one or more of the tissue-coupling elements may be designed to facilitate coupling of the connector 170 to patient tissue via one or more fasteners. The tissue-coupling elements can be disposed on or in one or more portions of the connector 170 (e.g., the connector housing or one or more of the connector flanges). Any suitable type of fastener (e.g., sutures, screws, pins, or the like or combinations thereof) can be used. It may be the case that it is preferred to couple the connector 170 to patient tissue without passing one or more fasteners through the connector housing 220. In which case, one or more lateral portions of the connector flanges 222 may provide surface areas for passing one or more fasteners through the connector flanges 222 and into patient tissue such that the one or more fasteners do not contact the connector housing 220.

FIGS. 6A-6B are schematic top views two additional embodiments of the connector 170. The connector 170 includes tissue-coupling elements 602 configured and arranged for facilitating coupling of the connector 170 to patient tissue via one or more fasteners. The tissue-coupling elements 602 are defined in the connector flanges 222. In FIG. 6A, the connector 170 includes two sets of connector flanges 222 positioned directly opposite the connector housing 220 from one another. In FIG. 6B, the connector 170 includes two connector flanges 222 positioned opposite the connector housing 220 from one another such that the connector flanges 222 are longitudinally offset from one another with respect to the longitudinal length 212 of the connector 170. In FIGS. 6A-6B, one tissue-coupling element 602 is defined in each of the connector flanges 222. It will be understood that any number of tissue-coupling elements 602 can be defined in any number of the connector flanges 222. It will also be understood that each of the connector flanges 222 can have any number of tissue-coupling elements 602 disposed thereon, or therein, including no tissue-coupling elements 602.

FIGS. 7A-7C shows several exemplary types of tissue-coupling elements 602 that are suitable for being disposed on, or in, one or more of the connector flanges 222. FIG. 7A is a schematic top close-up view of one embodiment of a mesh matrix 702 disposed in the connector flange 222. The mesh matrix 702 is configured and arranged to facilitate suturing the connector flange 222 to patient tissue without the medical practitioner needing to form apertures in the material forming the connector 170. Optionally, the mesh matrix 702 may also be configured and arranged to promote tissue ingrowth. The mesh matrix 702 can be formed from any suitable material including, for example, polyethylene terephthalate.

FIG. 7B is a schematic top close-up view of one embodiment of a ring 704 disposed in the connector flange 222. In preferred embodiments, the ring 704 is more rigid than the one or more materials used to form the connector flange 222 on which the ring 704 is disposed. The ring 704 is configured and arranged for receiving a fastener 706, such as a bone screw, or the like without a medical practitioner needing to manually form an aperture in the connector 170 during implantation, which may potentially lead to ripping or tearing of material of the connector 170. The ring 704 can be formed from any suitable material including, for example, stainless steel, titanium, PEEK, or the like.

FIG. 7C is a schematic top close-up view of one embodiment of a plurality of ports or recesses, such as port or recess 708 defined in the connector flange 222. In FIG. 7C, the plurality of ports or recesses 708 are configured and arranged for promoting tissue ingrowth over the implantable lifetime of the lead extension 130. It will be understood that the connector 170 can utilize any of the above-mentioned exemplary tissue-coupling elements 702, 704, and 706 in any combination on one or more of the connector flanges 222 of the connector 170.

Figure 8B:
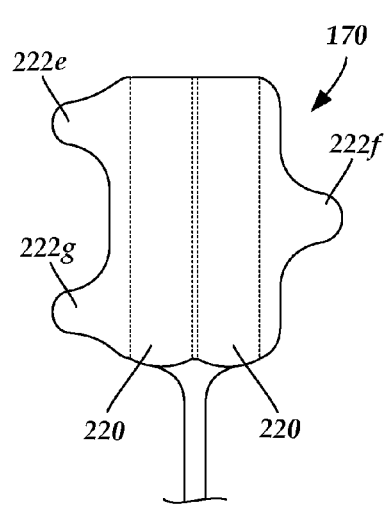
FIG. 8B is a schematic top view of one embodiment of the connector of FIG. 8A, the connector including a connector housing configured and arranged to receive multiple leads, according to the invention.
Figure 8C:
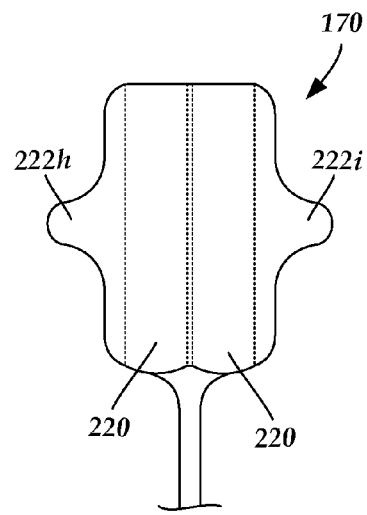
FIG. 8C is a schematic top view of another embodiment of the connector of FIG. 8A, the connector including a connector housing configured and arranged to receive multiple leads, according to the invention.

Efficacious deep brain stimulation sometimes involves using multiple leads to provide therapy to a patient. In which case, it may be advantageous to couple more than one lead to the lead extension. FIG. 8A is a schematic transverse cross-sectional view of an embodiment of two connector ports 230*a* and 230*b* disposed in the connector housing 220 of the connector 170. FIG. 8B is a schematic top view of one embodiment of two connector ports 230*a* and 230*b* disposed in the connector housing 220 of the connector 170. FIG. 8C is a schematic top view of another embodiment of two connector ports 230*a* and 230*b* disposed in the connector housing 220 of the connector 170. The connectors 170 can include any suitable number of connector flanges 22 arranged into any suitable configuration. In FIG. 8B, the connector 170 is shown with the connector flanges 222*g-i*, as shown in FIG. 4C. In FIG. 8C, the connector 170 is shown with the connector flanges 222*j,k*, as shown in FIG. 4D. In preferred embodiments, connector contacts 240 (not shown in FIGS. 8A-8C for clarity of illustration) are disposed in each of the connector ports 230*a* and 230*b*.

Figure 9:
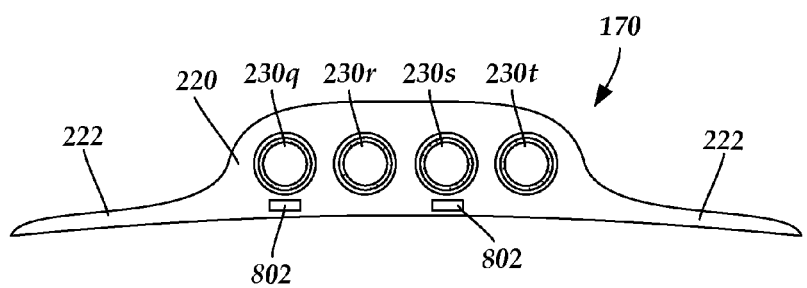
FIG. 9 is a schematic transverse cross-sectional view of another embodiment of the connector of FIG. 1, the connector including a connector housing configured and arranged to receive more than two leads, according to the invention.

The connectors 170 may, optionally, include more than two connector ports. FIG. 9 is a schematic transverse cross-sectional view of yet another embodiment of four connector ports 230*q*, 230*r*, 230*s*, and 230*t* disposed in the connector housing 220 of the connector 170. The connector ports 230*q-t* can be arranged in any suitable configuration. In preferred embodiments, the connector ports 230*q-t* are arranged in a single layer.

Optionally, one or more of the plurality of connector ports 230*a,b* or 230*q-t* can be labeled using at least one port identifier 802 (see e.g., FIGS. 8A and 9) disposed in proximity to a corresponding connector port, or group of connector ports, of the plurality of connector ports 230*a,b* or 230*q-t*. The at least one port identifier 802 can be formed using any suitable symbol, number, letter, code, nomenclature, texture, color, shape, material, or the like. In at least some embodiments, the at least one port identifier 802 is formed as a feature. The feature can be formed from any suitable material including, for example, one or more of stainless steel, tantalum, titanium, or the like.

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead extension for an electrical stimulation system, the lead extension comprising:
   a lead extension body having a first end and an opposing second end, the lead extension body comprising at least one tail;
   a plurality of lead extension terminals disposed on the second end of the lead extension body such that at least one of the plurality of lead extension terminals is disposed on each of the at least one tails;
   a connector having a first end, a second end opposite to the first end, a first side that connects the first end to the second end, and a second side that connects the first end to the second end and is opposite to the first side, the connector having a longitudinal axis extending between the first end and the opposing second end, the second end of the connector coupled to the first end of the lead extension body, the connector comprising
      a connector housing defining at least one connector port open along the first end of the connector and extending along the longitudinal axis of the connector towards the second end of the connector, each of the at least one connector ports configured and arranged to receive a proximal end of a lead,
      a plurality of connector contacts disposed in the connector port, the connector contacts configured and arranged to electrically couple to terminals of a lead when the lead is received by the connector housing,
      a first connector flange extending directly outwardly from the connector housing along the first side of the connector, and
      a second connector flange extending directly outwardly from the connector housing along the second side of the connector, wherein the first connector flange and the second connector flange are tapered in a direction extending away from the connector housing to reduce thickness of the first and second connector flanges; and
   a plurality of conductors extending along a length of the lead extension body, wherein each of the conductors electrically couples at least one of the lead extension terminals to at least one of the plurality of connector contacts.

2. The lead extension of claim 1, wherein the first connector flange comprises at least one tissue-coupling element.

3. The lead extension of claim 2, wherein the at least one tissue-coupling element is configured and arranged to promote tissue ingrowth.

4. The lead extension of claim 2, wherein the at least one tissue-coupling element is configured and arranged to couple the connector to patient tissue using at least one suture.

5. The lead extension of claim 2, wherein the at least one tissue-coupling element is configured and arranged to couple the connector to patient tissue using at least one screw.

6. The lead extension of claim 2, wherein the at least one tissue-coupling element comprises at least one ring.

7. The lead extension of claim 2, wherein the at least one tissue-coupling element comprises at least one mesh matrix.

8. The lead extension of claim 2, wherein the at least one tissue-coupling element comprises at least one recess defined in an outer surface of the first connector flange.

9. The lead extension of claim 1, wherein at least two connector ports are defined in the connector housing.

10. The lead extension of claim 1, wherein the connector housing comprises at least one tissue-coupling element configured and arranged to promote tissue ingrowth.

11. The lead extension of claim 1, wherein the first connector flange and the second connector flange are disposed on the connector such that the first connector flange and the second connector flange are positioned directly across the connector housing from one another with respect to the longitudinal axis of the connector.

12. The lead extension of claim 1, wherein the first connector flange and the second connector flange are disposed on the connector such that the first connector flange and the second connector flange are staggered from one another with respect to the longitudinal axis of the connector.

13. The lead extension of claim 1, wherein the connector further comprises a third connector flange permanently coupled to, and extending outwardly from, the connector housing along the first side of the connector, the third connector flange longitudinally offset from the first connector flange along the longitudinal axis of the connector.

14. The lead extension of claim 13, wherein the third connector flange is longitudinally offset from the second connector flange along the longitudinal axis of the connector.

15. The lead extension of claim 13, wherein the third connector flange is longitudinally even with the second connector flange along the longitudinal axis of the connector.

16. An electrical stimulation system comprising:
   the lead extension of claim 1;
   a lead configured and arranged for insertion into the at least one connector port of the lead extension, the lead comprising
      a lead body having a distal end, a proximal end, and a longitudinal length,
      a plurality of electrodes disposed on the distal end of the lead body,
      a plurality of lead terminals disposed on the proximal end of the lead body, and
      a plurality of conductors electrically coupling at least one of the electrodes to at least one of the lead terminals, the plurality of conductors extending along the longitudinal length of the lead body; and
   a control unit coupleable to the second end of the lead extension body, the control unit configured and arranged for providing stimulation to the plurality of electrodes of the lead.

17. A method for stimulating patient tissue, the method comprising
   providing the electrical stimulation system of claim 16;
   inserting the lead of the electrical stimulation system partially within the skull of a patient such that the electrodes of the lead are within the patient's skull and the terminals of the lead are external to the skull;
   disposing the lead extension connector of the electrical stimulation system over the patient's skull such that the first connector flange lies flat against the patient's skull;
   inserting the terminals of the lead into the at least one connector port of the lead extension connector;
   coupling the second end of the lead extension body to the control unit; and
   stimulating patient tissue using the electrodes of the lead using electrical pulses generated within the control unit.

18. The method of claim 17, further comprising securing the lead extension connector to patient tissue using at least one tissue-coupling element configured and arranged for promoting tissue ingrowth.

19. The method of claim 17, further comprising securing the lead extension connector to patient tissue using at least one tissue-coupling element configured and arranged for fastening the lead extension connector to patient tissue using at least one fastener.

* * * * *